United States Patent
Malabarba et al.

(10) Patent No.: US 7,655,676 B2
(45) Date of Patent: Feb. 2, 2010

(54) USE OF AMIDE DERIVATIVE OF GE 2270 FACTOR $A_3$ FOR THE TREATMENT OF ACNE

(75) Inventors: Adriano Malabarba, Binasco (IT); Marco Cavaleri, Saronno (IT); Giorgio Mosconi, Pieve Emanuele (IT); Daniela Jabes, Cassina Rizzardi (IT); Gabriela Romano, Legnano (IT)

(73) Assignee: Naicons S.C.A.R.L., Milan (IT)

( * ) Notice: Subject to any disclaimer, the term of this patent is extended or adjusted under 35 U.S.C. 154(b) by 869 days.

(21) Appl. No.: 10/518,802

(22) PCT Filed: Jun. 6, 2003

(86) PCT No.: PCT/EP03/05989

§ 371 (c)(1),
(2), (4) Date: Aug. 8, 2005

(87) PCT Pub. No.: WO03/105881

PCT Pub. Date: Dec. 24, 2003

(65) Prior Publication Data
US 2007/0117825 A1    May 24, 2007

(30) Foreign Application Priority Data
Jun. 17, 2002   (EP)   .................. 02013268

(51) Int. Cl.
*A61K 31/44* (2006.01)
*A01N 43/78* (2006.01)
*C07D 277/60* (2006.01)
*C07D 417/00* (2006.01)
*C07D 513/00* (2006.01)

(52) U.S. Cl. ................ 514/342; 514/366; 548/148; 546/270.1

(58) Field of Classification Search ................ 514/342, 514/366; 548/148; 546/270.1
See application file for complete search history.

(56) References Cited

U.S. PATENT DOCUMENTS

| 5,139,778 | A | 8/1992 | Selva et al. |
| 5,200,429 | A | 4/1993 | Sato et al. |
| 5,380,763 | A | 1/1995 | Sato et al. |
| 5,599,791 | A | 2/1997 | Tavecchia et al. |
| 6,008,225 | A | 12/1999 | Lociuro et al. |
| 6,143,739 | A | 11/2000 | Seneci et al. |

FOREIGN PATENT DOCUMENTS

| EP | 0494078 | 7/1992 |
| EP | 0577356 | 1/1994 |
| EP | 0565567 | 1/1995 |
| WO | WO 92/12172 | 7/1992 |

OTHER PUBLICATIONS

Clark, *Practitioner* 1993; 237:160-164.

Cunliffe, "The sebaceous gland and acne—40 years on," *Dermatology* 1998; 9-15.
Eady, "Bacterial resistance in acne," *Dermatology* 1998; 196:1:59-66.
Kelly, "Acne and related disorders," In: Sams JR., Lynch WM., Lynch PJ., eds. *Principles and practice of dermatology.* 2nd ed. New York, NY: Churchill Livingstone. 1996; 801-808.
Lancaster Catalog, pp. 589, 590, 1991 Windhan, N. H.
Toyoda et al., "An overview of topical antibiotics for acne treatment," *Dermatology* 1998; 196: 1:130-4.
Wu et al., "Role of anxiety and anger in acne patients: a relationship with the severity of the disorder," *J Am Acad Dermatol* 1988; 18: 325-333.

(Continued)

*Primary Examiner*—Shengjun Wang
*Assistant Examiner*—Kendra D Carter
(74) *Attorney, Agent, or Firm*—Nixon & Vanderhye P.C.

(57) ABSTRACT

Use of the compound of formula (I) and the pharmaceutically acceptable addition salts thereof for the manufacture of a medicament for topical treatment or 5 prevention of acne formula (I) wherein: R represents methoxymethyl, R1 represents methyl, Rz represents methyl, Y represents the group formula (II) The compound of formula (I) and the pharmaceutically acid addition salts thereof show selective activity against *propionibacterium acne* and are suitable for use in a method of treatment or prevention of acne.

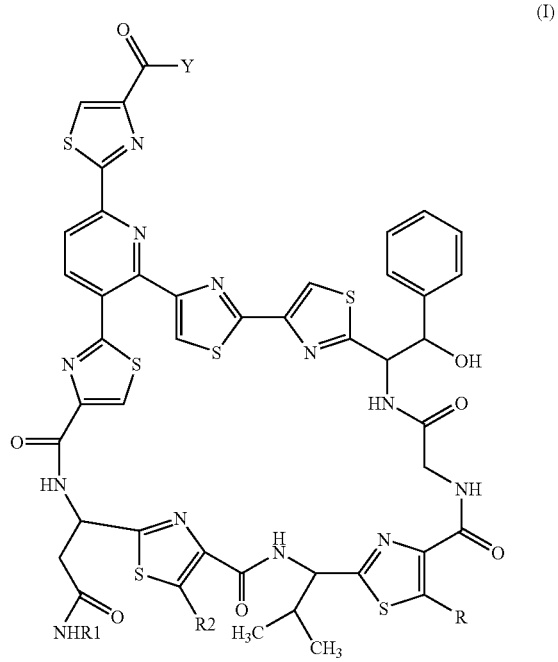

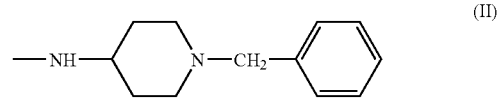

20 Claims, No Drawings

OTHER PUBLICATIONS

Berson DS, Shalita AR. The treatment of acne: the role of combination therapies. J Am Acad Dermatol 1995; 32: 531-541.

Crawford WW, Crawford IP, Stoughton RB, Cornell RC. Laboratory induction and clinical occurrence of combined clindamycin and erythromycin resistance in Corynebacterium acnes. J Invest Dermatol 1979; 72: 187-190.

Eady EA, Cove JH, Holland KT, et al. Erythromycin resistant propionibacteria in antibiotic-treated patients: association with therapeutic failure. Br J Dermatol 1989; 121:51-7.

Ebling FJ., Cunliffe WJ. Disorders of sebaceous glands. In: Rook A., Wilkinson DS., Ebling FJ., Champion RH., Burton JL, eds. Textbook of Dermatology. vol. III. Boston: Blackwell Scientific, 1992; 1699-744.

Espersen F. Resistance to antibiotics used in dermatology practice. BR J Dermatol 1998; 139 (53): 4-8.

Hurwitz S. The combined effect of vitamin A acid and benzoyl peroxide in the treatment of acne. Cutis 1976; 17: 585-590.

Ingram E, Holland KT, Gowland C, et al. Studies of the extracellular proteolytic activity produced by Propionibacterium acnes. J Appl Bacteriol 1983; 54:263-271.

Koo JYM, Smith LL. Psychologic aspects of acne. Pediatr Dermatol 1991; 8: 185-88.

Koo J. The psychosocial impact of acne: patients' perceptions. J Am Acad Dermatol 1995; 32: S26-S30.

Leyden JJ, McGinley KJ, Cavalieri S et al. Propionibacterium acnes resistance in acne patients. J Am Acad Dermatol 1983; 8: 41-5.

Leyden JJ. New understanding of the pathogenesis of acne. J Am Acad Dermatol 1995; 32: S15-S25.

McEvoy GK, ed. AHFS drug Information. Bethesda, MD: American Society of Health System Pharmacists; 1996; pp. 374 and 2522.

Nord CE. Treating acne with antibiotics leads to antibiotic resistance. Proceedings of the101st Annual Meeting of ASM, Orlando May 2001.

Panzer, J.D. et al. "Acne Treatment: A Comparative Efficacy Trial of Clindamycin and Tetracycline", Cutis, Excerpta Medica 19(1): 109-111 (Jan. 1977).

Puhvel SM, Sakamoto M. An in vitro evaluation of the inflammatory effect of purified comedonal components in human skin. J Invest Dermatol 1977; 69:401-406.

Ross JI, Snelling AM, Eady EA, Cove JH, Cunliffe WJ et al. Phenotypic and genotypic characterization of antibiotic-resistant Propionibacterium acnes isolated from acne patients attending dermatology clinics in Europe, the U.S.A., Japan and Australia. Br J Dermatol 2001; 144: 339-46.

Selva, E. et al. "Antibiotic GE 2270 a: a novel inhibitor of bacgerial protein synthesis. I. Isolation and characterization." J. Antibiotics (Tokyo) 44(7): 693-701 (1991).

Siegle RJ, Fekety R, Sarbone PD, et al. Effects of topical clindamycin on intestinal microflora in patients with acne. J Am Acad Dermatol 1986; 15: 180-5.

Sykes NL, Webster GF. Acne: a review of optimum treatment. Drugs 1994; 48: 59-70.

Walters CE, Ingham E, Eady EA, Cove JH, Kearney JN, Cunliffe WJ. In vitro modulation of keratinocyte-derived interleukin-1 alpha (IL-1 alpha) and peripheral blood mononuclear cell-derived IL-1 beta release in response to cutaneous commensal microorganisms. Infect Immun 1995; 63:1223-28.

Webster GF. Inflammation in Acne vulgaris. J Am Acad Dermatol 1995; 33:247-253.

Winston MH., Shalita AR. Acne vulgaris: pathogenesis and treatment. Pediatr Clinic North Am 1991; 38:889-903.

USE OF AMIDE DERIVATIVE OF GE 2270 FACTOR A₃ FOR THE TREATMENT OF ACNE

This is a national stage application of international application no. PCT/EP03/05989, filed Jun. 6, 2003, which in turn claims priority to European Application No. 02013268.4, filed Jun. 17, 2002. All of the above applications are expressly incorporated herein by reference in their entirety.

The object of this invention is to provide a medicament for the treatment or prevention of acne.

More particularly, the scope of this invention relates to the use of the compound of formula (I)

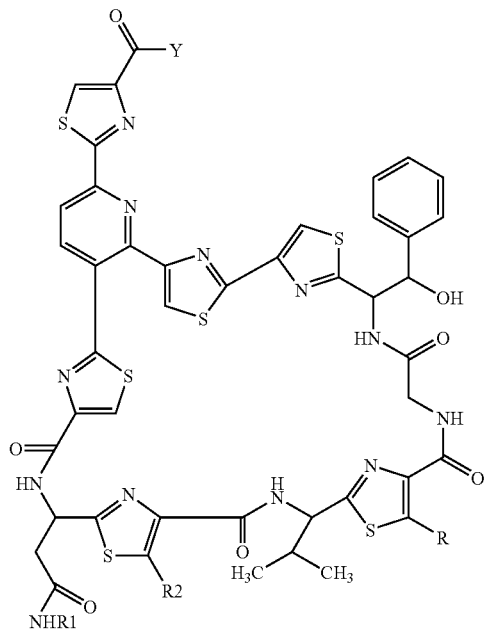

wherein:
R represents methoxymethyl,
$R_1$ represents methyl,
$R_2$ represents methyl,
Y represents the group

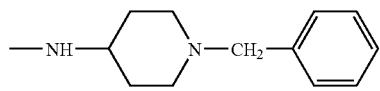

and the pharmaceutically acceptable acid addition salts thereof;
for the manufacture of a medicament for the topical treatment or prevention of acne.

A further object of the invention is a method for topical treatment of acne in a mammal suffering of said skin disorder which comprises topically administering the compound of formula (I) above and the pharmaceutically acceptable acid addition salts thereof to said mammal in an amount sufficient to provide inhibitory activity on proliferation of *Propionibacterium acnes*.

With the term "pharmaceutically acceptable acid addition salts", as used in this description and claims, are intended those salts with acids which from biological, manufacturing and formulation standpoint are compatible with the pharmaceutical practice.

Representative and suitable acid addition salts of the compounds of formula (I) include those salts formed by standard reaction with both organic and inorganic acids such as, for example, hydrochloric, hydrobromic, sulphuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, dodecanesulfonic acid benzenesulfonic, sorbic, picric, benzoic, cinnamic and the like.

The compound of formula (I) above is a known amide derivative of antibiotic GE 2270 factor $A_3$. This latter compound, which corresponds to the compound of formula (I) above wherein Y represent a group hydroxy, is also a known compound. Said amide derivative of antibiotic GE 2270 factor $A_3$ of formula (I), its preparation by amidation of antibiotic GE 2270 factor $A_3$, as well as the preparation of its pharmaceutically acceptable acid addition salts is described in U.S. Pat. No. 5,599,791.

Acne vulgaris, the most common chronic skin condition seen by dermatologists, is a disorder of the pilosebaceous unit characterized by papules, comedones and pustules. The face, back and chest are the areas most commonly affected as they posses a large number of sebaceous glands, about nine times the concentration found elsewhere on the body[1]. It affects more than seventeen million people in the US and it has been estimated that 85 percent of the adolescent population experiences this condition. Acne affects both genders with a peak incidence at 14-17 years for girls and 16-19 years for boys[2]. It also affects 8 percent of 25-34 years-old and 3 percent of 35-44 years-old adults[3]. However, the number of patients over the age of 25 objected by acne vulgaris is increasing. Adult women, in particular, may be affected and may experience premenstrual flares. In any case, severe acne tends to be more common in adolescent males then in people of other age-groups.

Although the primary cause of acne is end-organ hyperresponsiveness to circulating androgens triggering sebum overproduction in the follicle, an important role is also played by secondary bacterial infection that is favoured by abnormal desquamation of follicular epithelium. The increased amount of sebum produced, combined with excessive numbers of desquamated epithelial cells from the walls of the sebaceous follicle, accumulates within and distends the follicle, resulting in the formation of a clinically unapparent precursor lesion of acne vulgaris called the microcomedone. There are several explanations for ductal hypercornification. These include the comedogenic effects of certain sebaceous lipids, an androgen-controlled defect, retinoid control, local cytokine modulation and the effects of ductal bacteria[4]. *Propionibacterium acnes* is a member of the resident bacterial flora and resides in sebaceous follicles. The anaerobic environment of the follicles that are plugged, indeed, particularly facilitate proliferation of *P. acnes* causing the release of chemotactic factors and proinflammatory mediators into the follicle and surrounding dermis leading to the inflammation[5],[6],[7]. Detailed investigation of cell types and adhesion molecules would support the view that the inflammation of acne is a normal type 4 response in the first 76 h[8],[9],[10].

The clinical manifestations of these pathophysiological events include non-inflammatory closed (blackhead) or open (whitehead) comedos, as well as inflammatory lesions, including papules, pustules, cysts and nodules[11].

Acne can be divided into mild, moderate and severe based on the number of lesions and the surface of skin involved. Mild acne is characterized by open and closed comedones sometimes accompanied by few superficial inflammatory lesions, moderate acne is characterized by increasing largely superficial inflammatory lesions with pustules that have the tendency to scar with time. Nodules and cysts with marked scarring characterize severe acne.

While acne is not a life threatening disease, it has been related to psychiatric morbidity for many years. Emotional stress can exacerbate acne, and patients with acne develop psychiatric problems as a consequence of their condition[12]. Psychiatric issues associated with acne include problems with self-esteem/self-confidence, body image, embarrassment/social withdrawal, depression, anxiety, anger, preoccupation with acne, frustration/confusion, limitations in lifestyle, and problems in family relationships[13),14]. Permanent scarring is another relevant consequence of acne.

The treatment and prevention of acne includes various topical and systemic therapies and is guided by the type of clinical lesions present. Successful management of acne requires also careful patient evaluation followed by consideration of several factors related to the patient, e.g. age, skin type, coexisting conditions, lifestyle, menstrual regularity. The ideal agent would target each of the pathogenic factors without producing adverse effects. However, no single topical therapeutic agent has yet emerged that is capable of ameliorating all of the factors involved in the etiopathogenesis of acne vulgaris. Topical therapy is often preferred because of its safety compared with others forms of treatments[15]. Current topical therapies include comedolytic agents such as tretinoin, adapalene, azelaic acid, tazarotene and salicylic acid; antimicrobial agents such as benzoyl peroxide; antibiotics such as clindamycin, erythromycin and tetracycline; and anti-inflammatory agents such as sodium sulfacetamide. Oral antibiotics are often added to the treatment regimen when acne does not respond satisfactorily to topical therapy. Other systemic treatments for more severe, recalcitrant acne include estrogens, antiandrogens, and isotretinoin.

The eradication of *P. acnes* constitutes a logical approach to effective treatment, since the mere presence of this organism partially defines the disorder[4]. Benzoyl peroxide exerts its bactericidal activity on *P. acnes* by generating reactive oxygen species in the sebaceous follicle[16]. It is very effective in combination with either topical antibiotics or tretinoin[17] The major adverse effect of benzoyl peroxide is local irritation, particularly pronounced at therapy initiation. Other recorded adverse effects include erythema, dryness and allergic contact dermatitis (1-3% of patients). Clothes bleaching may present a problem in case of application to the chest or to the back.

Topical erythromycin and clindamycin have similar efficacy in patients with acne and are useful in the treatment of mild to moderate acne[18] These agents are available in a variety of formulations and are applied once or twice daily. They are often used in combination with benzoyl peroxide or tretinoin. Topical antibiotics are associated with some minor skin irritation, may be influenced by the vehicle used. Diarrhea and pseudomembranous colitis have been associated with the use of topical clindamycin[19), 20].

One of the biggest concerns with the use of antibiotics in acne therapy is the emergence of resistant strains of *P. acnes* and of other Gram-positive bacteria of the resident flora. *P. acnes* resistance is now accepted as clinical issue of increasing importance[5]. Combined resistance to erythromycin and clindamycin was first reported in 1979 in the USA in 20% of follicular *P. acnes* isolates from acne patients treated with topical formulations of either drug[21], while resistance of *P. acnes* to tetracyclines was first documented in 1983 in USA in patients who were not responding well to oral antibiotic treatment[22]. At present, it has been estimated that 1 in 4 acne patients harbour *P. acnes* strains resistant to clindamycin, erythromycin, and/or tetracycline[23]. In 1997, 65% of 567 acne patients in UK carried resistant *P. acnes* strains[24]. In a recent study, antibiotic-resistant *P. acnes* strains were found in 28% of acne patients previously treated with antibiotics compared with only 6% of acne patients not receiving antibiotic treatment[25]. It has also been demonstrated that *P. acnes* strains resistant to erythromycin, clindamycin, tetracycline and a variety of related antibiotics are to be found in Europe, USA, Australia and Japan[26]. The presence of erythromycin-resistant propionibacteria on the skin surface has been shown to correlate very strongly with inadequate response during therapy with oral erythromycin[27]. Besides, it is well documented that resistant strains of coagulase-negative staphylococci within the resident skin flora increase in both prevalence and population density as duration of topical antibiotic therapy of acne increases. Acne patients represent a considerable reservoir of resistant strains of these important nosocomial pathogens which can be transferred to close contacts[24].

Another drawback of currently used broad spectrum antibiotics is their poor selectivity of action against *P. acnes*, as they are active against all other Gram-positive bacteria which normally colonize the skin. This results in the eradication of these organisms whose presence on the skin is an obstacle to and generally prevents colonization by other problematic organisms: potentially, the elimination of resident Gram-positive bacteria may favour side infections caused by difficult-to-treat Gram-negative bacteria and pathogenic fungi.

It follows a need for a new antibiotic, possibly provided with novel mechanism of action, active against strains of *P. acnes* both susceptible and resistant to currently used antibacterial agents; further improvement on current therapy could be achieved with an antibiotic highly selective for *P. acnes* because of the lower possibility of skin side infections; low frequency of selection of resistant mutants and bactericidal activity would be additional advantages which could further recommend the use of such antibacterial agent.

The selectivity of action against *P. acnes* should allow maintaining almost unchanged the normal Gram-positive bacterial flora of the follicles, mainly staphylococci, thus preventing possible site colonization by other disease-causing bacteria, including Gram-negative pathogens, and fungi.

Selectivity of action against *P. acnes* is defined as a condition where the anti-acne candidate compound to be used in the treatment or prevention of acne, at the dosage which is usually employed in the topical formulations to provoke inhibition of proliferation of *P. acnes* on the skin, is inactive against all other Gram-positive bacteria, which normally colonize the skin surface thus contributing to the maintenance of its physiological conditions. In particular, bacterial strains which should not be affected by topical administration of the anti-acne candidate compound are *Staphylococcus aureus, Staphylococcus epidermidis*, and *Streptococcus pyogenes* strains. A pre-requisite to achieve a reasonable certainty that the above condition of selectivity of action is met, is that the anti-acne candidate compound shows in a series of in vitro tests MIC (Minimum Inhibitory Concentration) values against the above mentioned strains which are much higher than those displayed against *Propionibacterium acnes* strains which are both sensible and resistant to other antibiotics which are currently employed in the treatment of skin disorders such as erythromycin and clindamycin.

This property in a therapeutic setting, i.e. topical treatment of acne, will allow application of amounts of the drug which will not substantially affect the normal Gram-positive bacterial flora of the skin, mainly staphylococci, thus preventing possible site colonization by other disease-causing bacteria, including Gram-negative pathogens, and fungi.

According to this invention it has been found that the profile of activity of this amide derivative of formula (I) demonstrates that the said compound selectively inhibits the growth of *P. acnes* at concentration that are more than 1000 times lower than those required to inhibit the growth of the above mentioned bacteria that are present on the surface of the normal skin, thus indicating that it is useful for selective antimicrobial therapy of mild/moderate acne via topical administration as mono-therapy or in association with agents that possess comedolytic and anticomedogenic activity. In fact, the compound of formula (I) has selective in vitro activity against *Propionibacterium acnes*, with MIC values ranging from 0.06 (80% of tested strains) to 0.25 mg/mL including isolates resistant to broader spectrum antibiotics, i.e. erythromycin, tetracyclin and clindamycin, which have been used extensively for the treatment of acne for over 30 years. Other Gram-positive species are not susceptible to the compound of formula (I), the only exception being enterococci, which are inhibited at concentrations ranging from 0.5 to 16 mg/mL. However, these strains have no relevance in the context of this invention since they are not part of the normal skin flora. The compound of formula (I) is inactive against Gram-negative bacteria and fungi.

The surprisingly high degree of selectivity action of the compound of formula (I) of this invention has been evidenced through in vitro tests wherein the minimum inhibitory concentration (MIC) against *Propionibacterium acnes* strains both sensitive and resistant to erythromycin and clindamycin and against a series *Staphylococcus* strains have been determined. The tests have been carried out in comparison with antibiotic GE 2270 and four representative compounds (B, C, D and E) described in U.S. Pat. No. 5,599,791.

The results are reported in TABLE 1 below

The data reported in the above TABLE confirm that all comparison compounds B, C, and D and GE 2270, although presenting the same level of activity of the amide compound of formula (I) of this invention (A) against *Propionibacterium acnes* strains, they are active also against all *Staphylococcus* strains tested, with MIC values ranging from 0.06 μg/ml to 8 μg/ml. This activity profile can justify the acknowledgement of a selectivity of action against the *Propionibacterium* strains.

The suitability of the compound of formula (I) for use in the treatment of acne vulgaris has been confirmed in a series of microbiological, toxicological and pharmacokinetic evaluations, the results of which are reported in the following.

In TABLE 2 below are summarized the results of a study of the microbiological activity of the amide compound of formula (I) against 15 isolates of *P. acnes* displaying resistance to clindamycin or erythromycin collected from patients affected by acne. TABLE 3 reports the activity data of the same amide compound of formula (I) against 5 clinical iso-

TABLE 1

| | | | MIC (μg/ml) | | | | |
|---|---|---|---|---|---|---|---|
| Microorganism | strain | medium | A | B | C | D | GE 2270 |
| *Staphylococcus aureus* | Smith ATCC 19636 | Mueller Hinton (MH) | >128 | 2 | 2 | 1 | 0.06 |
| *Staphylococcus aureus* | Smith ATCC 19636 | MH + 30% bovine serum | >128 | 8 | 8 | 4 | 0.25 |
| *Staphylococcus aureus* | MRSA | MH | >128 | 4 | 2 | 0.250 | <0.125 |
| *Staphylococcus epidermidis* | ATCC 12228 | MH | >128 | 8 | 4 | 0.5 | <0.125 |
| *Streptococcus pyogenes* | C 203 | MH | >128 | >128 | >128 | 8 | 0.25 |
| *Propionibacterium acne* | ATCC 6919 | Wilkins Chalgren (WC) | <0.125 | <0.125 | <0.125 | <0.125 | <0.125 |
| *Propionibacterium acne* | ATCC 6922 | WC | <0.125 | <0.125 | <0.125 | 0.125 | <0.125 |
| *Propionibacterium acne* | ATCC 25746 | WC | <0.125 | <0.125 | <0.125 | <0.125 | <0.125 |
| *Propionibacterium acne* | clinical isolate | WC | <0.125 | <0.125 | <0.125 | <0.125 | <0.125 |
| *Propionibacterium acne* | clinical isolate | WC | <0.125 | <0.125 | <0.125 | <0.125 | <0.125 |
| *Propionibacterium acne* | clinical isolate | WC | <0.125 | <0.125 | <0.125 | 0.125 | 0.125 |
| *Propionibacterium acne* | clinical isolate | WC | <0.125 | <0.125 | <0.125 | <0.125 | <0.125 |
| *Propionibacterium acne* | clinical isolate | WC | <0.125 | <0.125 | <0.125 | <0.125 | <0.125 |
| *Propionibacterium acne* | clinical isolate | WC | <0.125 | <0.125 | <0.125 | <0.125 | <0.125 |
| *Propionibacterium acne* | clinical isolate | | <0.125 | <0.125 | <0.125 | <0.125 | <0.125 |

A: Compound of formula (I);
B: Compound of Example 10 of U.S. Pat. No. 5.599.791;
C: Compound of Example 12 of U.S. Pat. No. 5.599.791;
D: Compound of Example 13 of U.S. Pat. No. 5.599.791 lates of *P. acnes* displaying sensitivity toward erythromycin and clindamycin.

TABLE 2

Summary of minimum inhibitory concentration values for erythromycin, clindamycin and compound of formula (I) against clinical isolates of *P. acnes* displaying antibiotic-resistant phenotypes

| | Erythromycin | | | Clindamycin | | | Compound of formula (I) | | |
|---|---|---|---|---|---|---|---|---|---|
| MIC μg/ml | N° isolates | Cumul. % | MIC 50/90 | N° isolates | Cumul. % | MIC 50/90 | N° isolates | Cumul. % | MIC 50/90 |
| 0.015 | | | | | | | | | |
| 0.03 | | | | | | | 9 | 60% | $MIC_{50}$ |
| 0.06 | | | | | | | 6 | 100% | $MIC_{90}$ |
| 0.125 | | | | | | | | | |
| 0.25 | | | | | | | | | |

TABLE 2-continued

Summary of minimum inhibitory concentration values for
erythromycin, clindamycin and compound of formula (I)
against clinical isolates of *P. acnes* displaying
antibiotic-resistant phenotypes

| MIC µg/ml | Erythromycin | | | Clindamycin | | | Compound of formula (I) | | |
|---|---|---|---|---|---|---|---|---|---|
| | N° isolates | Cumul. % | MIC 50/90 | N° isolates | Cumul. % | MIC 50/90 | N° isolates | Cumul. % | MIC 50/90 |
| 0.5 | | | | | | | | | |
| 1 | | | | | | | | | |
| 2 | | | | | | | | | |
| 4 | | | | 3 | 20% | | | | |
| 8 | | | | 2 | 33% | | | | |
| 16 | | | | 0 | | | | | |
| 32 | | | | 0 | | | | | |
| 64 | | | | 8 | 87% | $MIC_{50}$ | | | |
| 128 | | | | 0 | | | | | |
| 256 | | | | 2 | 100% | $MIC_{90}$ | | | |
| 512 | 1 | 7% | | | | | | | |
| 1024 | 11 | 80% | $MIC_{50}$ | | | | | | |
| 2048 | 3 | 100% | $MIC_{90}$ | | | | | | |

TABLE 3

Summary of minimum inhibitory concentration values for
erythromycin, clindamycin and compound of formula (I)
against clinical isolates of *P. acnes* displaying
antibiotic-sensitive phenotypes

| MIC µg/ml | Erythromycin | | | Clindamycin | | | Compound of formula (I) | | |
|---|---|---|---|---|---|---|---|---|---|
| | N° isolates | Cumul. % | MIC 50/90 | N° isolates | Cumul. % | MIC 50/90 | N° isolates | Cumul. % | MIC 50/90 |
| 0.015 | | | | | | | | | |
| 0.03 | | | | | | | 4 | 80% | |
| 0.06 | | | | | | | 1 | 100% | |
| 0.125 | 5 | 100% | $MIC_{90}$ | 3 | 60% | $MIC_{50}$ | | | |
| 0.25 | | | | 1 | 80% | | | | |
| 0.5 | | | | 1 | 100% | $MIC_{90}$ | | | |
| 1 | | | | | | | | | |

$MIC_{50}$ and $MIC_{90}$ means minimum inhibitory concentration capable of inhibiting 50% and 90%, respectively, of the strains tested.

The above TABLES 2 and 3 shows that the compound of formula (I) is as active against erythromycin and clindamycin resistant *P. acne* strains as is active against antibiotic sensitive *P. acne* strains. To determine the frequency of selection of *P. acne* mutants, resistant to the compound of formula (I), the same compound was incorporated into solid medium at 1 and 10 µg/ml and bacterial suspensions of approximately $10^{10}$ CFU were distributed on the plate surface. Based on the number of grown colonies, the frequency of resistance to the compound of formula (I) ranged form $1.4 \times 10^{-9}$ to $1.5 \times 10^{-10}$ at 1 µg/mL and from $3.3 \times 10^{-9}$ to $9.4 \times 10^{-10}$ at 10 µg/ml.

Dermal administration tests of the compound of formula (I) show that the absorption of the said compound through the skin is very low or null.

Topical absorption was assessed both with the 3% gel formulation of Example 6 below and with a 3% polyethylene glycol 400 solution.

Studies in rabbits with the 3% gel formulation showed measurable plasma concentrations of the test compound after 7 days of daily applications only in a limited number of samples, indicating minimal, if any, absorption. In a 28 days tolerability study on both scarified and non-scarified skin in rabbits, the 3% gel showed no detectable plasma levels throughout the whole study.

According to this invention the compound of formula (I) can be incorporated into a variety of formulations suitable for topical delivery of active ingredients. The topical formulations suitable for topical treatment and prevention of acne vulgaris are creams, lotions, mousses, sprays, emulsions, gels and the like, which are manufactured according to methods commonly known in the art (see, for instance: *Topical Formulations: Design and Development*—Bozena Michniak/Paperback/CRC Press, LLC/February 1999; *Remington: The Science and Practice of Pharmacy* 20th—Alfonso L. Gennaro, Alfonso R. (Ed.) Gennaro; Publisher: Lippincott Williams & Wilkins, December 2000, 20th Ed.; *Encyclopedia of Pharmaceutical Technology*—James Swarbrick (Editor), James C. Boylan (Editor)/Hardcover/Marcel Dekker/May 1997).

In said formulations, the amide derivative of antibiotic GE 2270 of formula (I) may optionally be associated with other components which have auxiliary action in the treatment and prevention of acne or may provide skin benefits. Examples of said additional components are, for instance, other ingredients active against proliferation of *Propionibacterium acnes*, e.g. antibiotics such as erythromycin, clindamycin and tetracyclines, antimicrobials such as chlorexidine and benzoylperoxide, synthetic or natural substances which have been described as possessing inhibitory activity against *P. acnes* such as 1-pentadecanol[28] and derivatives thereof[29], cedrene, caryophyllene, longifolene and thujopsene[30], comedolytic agents such as tretinoin, adapalene, azelaic acid, tazarotene, salicylic acid and derivatives thereof, antinflammatory agents such as NSAID (e.g. acetylsalicylic acid, ibuprofen, naproxen, sulfacetamide), steroidal antinflammatory agents (e.g. hydrocortisone), vitamins (e.g. retinoic acid and derivatives thereof), oil or sebum control agents (e.g. clay silicones), skin healing agents, and skin conditioning agents.

In general the amount of the above compound of formula (I) of this invention in the topical composition for treating or preventing acne according to this invention may range from about 0.1% (w/w) to about 10% (w/w).

The topical compositions useful for delivery of the compound of formula (I) contains the usual pharmaceutically acceptable excipients, including those having carrier, vehicle, or other delivery functions, preservative agents, surface active agents, moisture retaining agent, thickeners, perfumes, chelating agents, water, alkyls, antioxidants, antiseptics, colorants and UV adsorbents.

Non limitative examples of topical compositions containing the amide derivative of antibiotic GE 2270 factor A are given herebelow with the purpose of illustrating the invention.

EXAMPLE 1

3% Cream

|  | Weight (percent) |
|---|---|
| Compound of formula (I), as hydrochloride | 3.000 |
| Sodium hydroxide | 0.102 |
| Benzyl alcohol | 0.850 |
| Sorbitan monostearate | 1.615 |
| Cetyl palmitate | 1.700 |
| Cetyl alcohol | 3.400 |
| Stearyl alcohol | 3.400 |
| Polysorbate 60 | 5.185 |
| Isopropyl myristate | 6.800 |
| Diethylene glycol monoethyl ether | 12.000 |
| Purified water | 61.948 |
|  | 100.00 |

EXAMPLE 2

3% Gel

|  | Weight (percent) |
|---|---|
| Compound of formula (I), as lactate | 3.000 |
| Hydroxyethyl cellulose | 2.500 |
| Diethylene glycol monoethyl ether | 47.000 |
| Purified water | 47.000 |
|  | 100.000 |

EXAMPLE 3

3% Alcoholic Gel I

|  | Weight (percent) |
|---|---|
| Compound of formula (I), as hydrochloride | 3.000 |
| Diethylene glycol monoethyl ether | 12.000 |
| Hydroxypropyl cellulose | 15.000 |
| Ethyl alcohol 96% | 70.000 |
|  | 100.000 |

EXAMPLE 4

3% Alcoholic Gel II

|  | Weight (percent) |
|---|---|
| Compound of formula (I) | 3.000 |
| Hydroxypropyl cellulose | 3.000 or 1.500 |
| Purified water | 9.500 |
| Lactic acid | 0.500 |
| Ethyl alcohol 95% | 84.000 or 85.500 |
| Cetyl alcohol | 100.000 |

EXAMPLE 5

3% Hydroalcoholic Lotion

|  | Weight (percent) |
|---|---|
| Compound of formula (I) | 3.000 |
| Lactic acid | 2.000 |
| Diethylene glycol monoethyl ether | 36.500 |
| Ethyl alcohol | 10.000 |
| Methyl p. hydroxybenzoate | 0.150 |
| Propyl p. hydroxybenzoate | 0.050 |
| Water | q.s. to 100 |

EXAMPLE 6

1,5% or 3% Gel

|  | Weight (percent) |
|---|---|
| Compound of formula (I) | 1.500 or 3.000 |
| Methyl cellulose | 1.500 |
| Diethylene glycol monoethyl ether | 35.000 |
| Ethyl alcohol 96% | 10.000 |
| Lactic acid | 2.000 |
| Methyl p. hydroxybenzoate | 0.150 |
| Propyl p. hydroxybenzoate | 0.050 |
| Purified water | q.s. to 100.000 |

EXAMPLES 7, 8 AND 9

0.1%, 1% and 0.5% Gels

| | Weight (percent) |
|---|---|
| 7) | |
| Compound of formula (I) | 0.100 |
| Alcohol SD 40 | 81.000 |
| Hydroxypropyl cellulose, zinc acetate, propylene glycol, diethylolamine lauramide, fragrances | q.s. to 100.000 |
| 8) | |
| Compound of formula (I) | 1.000 |
| Alcohol SD 40-2 | 77.000 |
| Propylene glycol, hydroxypropyl cellulose | q.s. to 100.000 |
| 9) | |
| Compound of formula (I) | 0.500 |
| Butylated hydroxytoluene, hydroxypropyl cellulose, ethyl alcohol | q.s. to 100.000 |

EXAMPLE 10

5% Cream

| | Weight (per cent) |
|---|---|
| Compound of formula (I) | 5,000 |
| Polyoxyethylene fatty acid esters, cetyl-stearyl octanoate, wax and glycerides mixture, glycol, propylene glycol, benzoic acid, purified water | q.s. to 100,000 |

EXAMPLE 11

5% Dermatological Suspension

| | Weight (percent) |
|---|---|
| Compound of formula (I) | 5.000 |
| Glycol, isostearyl alcohol, cetyl-stearyl alcohol, stearic acid, glyceryl monostearate, sodium lauroyl sarcosinate, methyl p-hydroxybenzoate, purified water | q.s. to 100.000 |

REFERENCES

1) Ebling F J., Cunliffe W J. Disorders of sebaceous glands. In: Rook A., Wilkinson D S, Ebling F J., Champion R H., Burton J L, eds. Textbook of dermatology. Vol III. Boston: Blackwell Scientific, 1992; 1699-744.

2) Practitioner 1993; 237:160-164.

3) Bergfeld W F, Odom R B. New Perspectives on acne. Clinicians 1996; 12:4.

4) Cunliffe W J. The sebaceous gland and acne—40 years on. Dermatology 1998; 9-15.

5) Leyden J J. New understanding of the pathogenesis of acne. J Am Acad Dermatol 1995; 32: S15-S25.

6) Winston M H., Shalita A R. Acne vulgaris: pathogenesis and treatment. Pediatr Clinic North Am 1991; 38:889-903.

7) Webster G F. Inflammation in acne vulgaris. J Am Acad Dermatol 1995; 33:247-253.

8) Ingham E, Holland K T, Gowland C, et al. Studies of the extracellular proteolytic activity produced by *Propionibacterium acnes*. J Appl Bacteriol 1983; 54:263-271.

9) Puhvel S M, Sakamoto M. An in vitro evaluation of the inflammatory effect of purified comedonal components in human skin. J Invest Dermatol 1977; 69:401-406.

10) Walters C E, Ingham E, Eady E A, Cove J H, Kearney J N, Cunliffe W J. In vitro modulation of keratinocyte-derived interleukin-1 alpha (IL-1 alpha) and peripheral blood mononuclear cell-derived IL-1 beta release in response to cutaneous commensal microorganisms. Infect Immun 1995; 63:1223-28.

11) Kelly A P. Acne and related disorders. In: Sams J R., Lynch W M., Lynch P J., eds. Principles and practice of dermatology. $2^{nd}$ ed. New York, N.Y.: Churchill Livingstone. 1996; 801-808.

12) Koo J Y M, Smith L L. Psychologic aspects of acne. Pediatr Dermatol 1991; 8: 185-88.

13) Koo J. The psychosocial impact of acne: patients' perceptions. J Am Acad Dermatol 1995; 32: S26-S30.

14) Wu S F, Kinder B N, Trunnel T N, Fulton J E. Role of anxiety and anger in acne patients: a relationship with the severity of the disorder. J Am Acad Dermatol 1988; 18: 325-333.

15) Toyoda M, Morohashi M. An overview of topical antibiotics for acne treatment. Dermatology 1998; 196: 1: 130-4.

16) Berson D S, Shalita A R. The treatment of acne: the role of combination therapies. J Am Acad Dermatol 1995; 32: 531-541.

17) Hurwitz S. The combined effect of vitamin A acid and benzoyl peroxide in the treatment of acne. Cutis 1976; 17:585-590.

18) Sykes N L, Webster G F. Acne: a review of optimum treatment. Drugs 1994; 48: 59-70.

19) McEvoy G K, ed. AHFS drug Information. Bethesda, Md.: American Society of Health System Pharmacists; 1996.

20) Siegle R J, Fekety R, Sarbone P D, et al. Effects of topical clindamycin on intestinal microflora in patients with acne. J Am Acad Dermatol 1986; 15: 180-5.

21) Crawford W W, Crawford I P, Stoughton R B, Cornell R C. Laboratory induction and clinical occurrence of combined clindamycin and erythromycin resistance in *Corynebacterium acnes*. J Invest Dermatol 1979; 72: 187-190.

22) Leyden J J, McGinley K J, Cavalieri S et al. *Propionibacterium acnes* resistance in acne patients. J Am Acad Dermatol 1983; 8: 41-5.

23) Espersen F. Resistance to antibiotics used in dermatology practice. Br J Dermatol 1998; 139 (53): 4-8.

24) Eady E. A. Bacterial resistance in acne. Dermatology 1998; 196:1:59-66.

25) Nord C E. Treating acne with antibiotics leads to antibiotic resistance. Proceedings of the 101st Annual Meeting of ASM, Orlando May 2001.

26) Ross J I, Snelling A M, Eady E A, Cove J H, Cunliffe W J et al. Phenotypic and genotypic characterization of antibiotic-resistant *Propionibacterium acnes* isolated from acne patients attending dermatology clinics in Europe, the U.S.A., Japan and Australia. Br J Dermatol 2001; 144: 339-46.

27) Eady E A, Cove J H, Holland K T, et al. Erythromycin resistant propionibacteria in antibiotic-treated patients: association with therapeutic failure. Br J Dermatol 1989; 121:51-7.
28) U.S. Pat. No. 5,380,763
29) EP 0577356
28) U.S. Pat. No. 5,380,763

The invention claimed is:
1. A medicament for use in the topical treatment of acne which comprises a compound of formula (I)

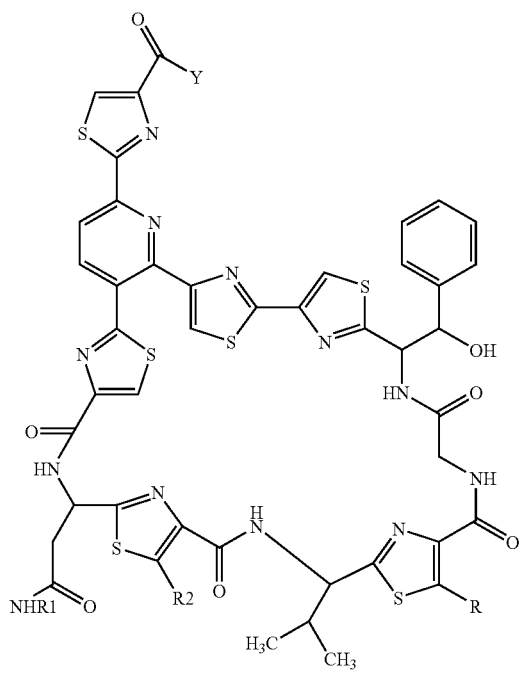

wherein:
R represents methoxymethyl,
$R_1$ represents methyl,
$R_2$ represents methyl,
Y represents the group

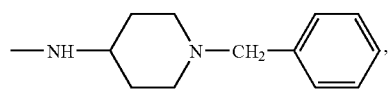

and the pharmaceutically acceptable acid addition salts thereof, wherein said compound inhibits the growth of *Propionibacterium acnes* strain at dosages that are inactive against gram-positive bacteria that normally colonize the skin surface.

2. The medicament as in claim 1, wherein the gram-positive bacteria that normally colonize the skin surface are selected from the group consisting of *Staphylococcus aureus, Staphylococcus epidermis*, and *Streptococcus pyogenes*.

3. The medicament as in claim 1, wherein the gram-positive bacteria that normally colonize the skin surface are resistant to a broader spectrum antibiotic.

4. A method for treating acne which comprises topically administering a compound of formula (I)

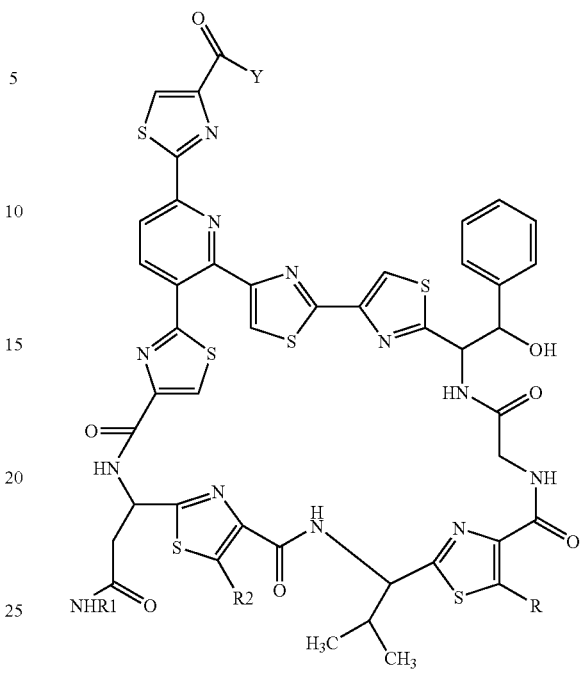

wherein:
R represents methoxymethyl,
$R_1$ represents methyl,
$R_2$ represents methyl,
Y represents the group

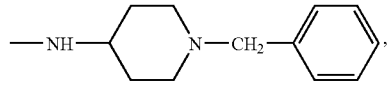

or a pharmaceutically acceptable acid addition salt thereof to a patient affected by or exposed to said skin disorder, in an amount sufficient to provide inhibitory activity or proliferation of *Propionibacterium acne*, wherein said compound inhibits the growth of *Propionibacterium acnes* strain at dosages that are inactive against other gram-positive bacteria that normally colonize the skin surface.

5. The method as in claim 4, wherein the gram-positive bacteria that normally colonize the skin surface are selected from the group consisting of *Staphylococcus aureus, Staphylococcus epidermis*, and *Streptococcus pyogenes*.

6. The method as in claim 4, wherein the gram-positive bacteria that normally colonize the skin surface are resistant to a broader spectrum antibiotic.

7. The method as in claim 6, wherein the broader spectrum antibiotic is selected from the group consisting of erythromycin, tetracycline, and clindamycin.

8. The method as in claim 4, further comprising the step of administering an additional component that has auxiliary action in the treatment of acne or provides skin benefits.

9. The method as in claim 8, wherein the additional component that has auxiliary action in the treatment of acne or provides skin benefits is selected from the group consisting of an antibiotic, antimicrobial, comedolytic agent, non-steroidal anti-inflammatory agent, steroidal anti-inflammatory agent, vitamin, oil or sebum control agent, skin healing agent, and skin conditioning agent.

10. The method as in claim 9, wherein the antibiotic is selected from the group consisting of erythromycin, tetracycline, and clindamycin.

11. The method as in claim 9, wherein the antimicrobial is selected from the group consisting of chlorexidine, benzoylperoxide, 1-pentadecanol, cedrene, caryophyllene, longifolene, thujopsene, and derivatives thereof.

12. The method as in claim 9, wherein the comedolytic agent is selected from the group consisting of tretinoin, adapalene, azelaic acid, tazarotene, salicylic acid, and derivatives thereof.

13. The method as in claim 9, wherein the non-steroidal anti-inflammatory agent is selected from the group consisting of acetylsalicylic acid, ibuprofen, naproxen, and sulfacetamide.

14. The method as in claim 9, wherein the steroidal anti-inflammatory agent is hydrocortisone.

15. The method as in claim 9, wherein the vitamin is retinoic acid.

16. The method as in claim 9, wherein the oil or sebum control agent is clay silicone.

17. The method as in claim 4, wherein the compound of formula (I) or a pharmaceutically acceptable acid addition salt thereof is incorporated into a pharmaceutical composition suitable for topical administration in an amount ranging from about 0.1 to 10 percent by weight of said pharmaceutical composition.

18. The method as in claim 17, wherein the pharmaceutical composition is in the form of a cream, lotion, mousse, spray, emulsion or gel.

19. The method as in claim 4, wherein the pharmaceutically acceptable acid addition salts are salts with hydrochloric acid or lactic acid.

20. The method as in claim 17, wherein the pharmaceutical composition includes a pharmaceutically acceptable excipient.

* * * * *

UNITED STATES PATENT AND TRADEMARK OFFICE
CERTIFICATE OF CORRECTION

PATENT NO.       : 7,655,676 B2                                      Page 1 of 1
APPLICATION NO. : 10/518802
DATED            : February 2, 2010
INVENTOR(S)      : Malabarba et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1213 days.

Signed and Sealed this

Twenty-eighth Day of December, 2010

David J. Kappos
*Director of the United States Patent and Trademark Office*